United States Patent
Kim et al.

(10) Patent No.: US 7,300,493 B2
(45) Date of Patent: Nov. 27, 2007

(54) APPARATUS AND METHOD FOR CONTROLLING AIR CLEANING

(75) Inventors: Ho Jung Kim, Inchun-si (KR); In Ho Choi, Kyungki-do (KR); Kwan Ho Yum, Seoul (KR); Ho Seon Choi, Seoul (KR)

(73) Assignee: LG Electronics Inc., Seoul (KR)

( * ) Notice: Subject to any disclaimer, the term of this patent is extended or adjusted under 35 U.S.C. 154(b) by 105 days.

(21) Appl. No.: 11/243,964

(22) Filed: Oct. 6, 2005

(65) Prior Publication Data

US 2006/0075893 A1    Apr. 13, 2006

(30) Foreign Application Priority Data

Oct. 8, 2004    (KR) .................. 10-2004-0080448

(51) Int. Cl.
*B03C 3/68*    (2006.01)

(52) U.S. Cl. ............... 95/2; 95/3; 95/81; 96/18; 96/19; 96/80; 323/903

(58) Field of Classification Search ........... 96/18, 96/19, 80; 95/2, 3, 80, 81; 323/903
See application file for complete search history.

(56) References Cited

U.S. PATENT DOCUMENTS

| | | | | |
|---|---|---|---|---|
| 2,642,149 A | * | 6/1953 | Backer et al. ............. | 96/19 |
| 3,049,848 A | * | 8/1962 | Klemperer ................ | 96/23 |
| 4,809,127 A | | 2/1989 | Steinman et al. | |
| 5,124,905 A | * | 6/1992 | Kniepkamp ............... | 363/19 |
| 5,278,492 A | * | 1/1994 | Huynh et al. ............. | 323/326 |
| 5,321,274 A | * | 6/1994 | Yeh et al. ................ | 250/573 |
| 5,542,964 A | | 8/1996 | Kroeger et al. | |
| 6,245,126 B1 | * | 6/2001 | Feldman et al. .......... | 95/59 |
| 6,375,714 B1 | * | 4/2002 | Rump et al. ............. | 95/3 |
| 6,461,405 B2 | * | 10/2002 | Reyes ..................... | 95/7 |
| 7,122,070 B1 | * | 10/2006 | Krichtafovitch .......... | 95/2 |
| 2001/0032544 A1 | * | 10/2001 | Taylor et al. ............ | 96/19 |

FOREIGN PATENT DOCUMENTS

| | | |
|---|---|---|
| DE | 101 11 445 A1 | 9/2002 |
| EP | 1 125 588 A2 | 8/2001 |
| EP | 1 293 216 A1 | 3/2003 |
| JP | 9-108318 A | 4/1997 |
| KR | 1999-0017482 U | 5/1999 |

* cited by examiner

*Primary Examiner*—Richard L. Chiesa
(74) *Attorney, Agent, or Firm*—Birch, Stewart, Kolasch & Birch, LLP

(57) ABSTRACT

Disclosed is an apparatus and method for controlling an air cleaning. The apparatus includes an air cleaning element, an AC high-voltage generator and a control unit. The air cleaning element generates negative ions and ozone using plasma discharge, and cleans indoor air using the negative ions and ozone. The AC high-voltage generator generates an AC high-voltage, and applies the AC high-voltage to the air cleaning element. The control unit varies at least one of the AC voltage and AC frequency applied to the air cleaning element by the AC high-voltage generator depending on a state of indoor air being cleaned using the air cleaning element. Therefore, it is possible to effectively generate negative ions while minimizing ozone generation to an acceptable level depending on a state of indoor air, thereby increasing air cleaning performance so as to sterilize and clean contaminants more efficiently.

8 Claims, 5 Drawing Sheets

APPARATUS AND METHOD FOR CONTROLLING AIR CLEANING

BACKGROUND OF THE INVENTION

1. Field of the Invention

The present invention relates to an air cleaning apparatus arranged within an air conditioner, an air cleaner, or the like, and more particularly to an apparatus and method for controlling air cleaning, which is capable of cleaning air by controlling an AC voltage or an AC frequency therein, depending on the pollution level of indoor air.

2. Description of the Related Art

An air cleaning apparatus generates a number of negative ions using an air cleaning element, and thereby cleans indoor air using such generated negative ions, wherein the air cleaning element is referred to as a negative ion generator of a surface discharge type which has recently been developed.

FIG. 1 is a block diagram showing the construction of a conventional air cleaning control apparatus, and FIG. 2 is a graph illustrating an operating control state of the conventional air cleaning control apparatus. Referring to FIGS. 1 and 2, the conventional air cleaning control apparatus using the above air cleaning element will be explained as follows.

The conventional air cleaning control apparatus includes, as shown in FIG. 1, a rectifier 3, a DC voltage generator 5, an air cleaning element 7 and a microcomputer 9. The rectifier 3 rectifies an AC voltage into a DC voltage, for example, it may rectify a commercial AC voltage of 220V into a 12V DC voltage. When the 12V DC voltage is supplied to the DC voltage generator 5, the DC voltage generator 5 supplies a high voltage to the air cleaning element 7 so as to generate negative ions.

As shown in FIG. 2, the microcomputer 9 generates ON/OFF signals in response to an operation signal and a stop signal manually inputted by a user, wherein the ON signal is converted into a high-voltage signal by the DC voltage generator 5, and the OFF signal is converted into a ground voltage signal by the DC voltage generator 5. Thus, any one of the high-voltage ON signal and the ground OFF signal is applied to the air cleaning element 7.

For example, when the microcomputer 9 supplies the ON signal to the DC voltage generator 5, the high-voltage ON signal is generated by the DC voltage generator 5. In addition, the high-voltage ON signal is applied to the air cleaning element 7, thereby generating negative ions by means of plasma discharge in the air cleaning element 7.

The negative ions generated in the air cleaning element 7 are supplied to indoor air passing through the vicinity of the vicinity of the air cleaning element 7, thereby cleaning indoor air.

However, the above conventional air cleaning control apparatus has a structure for merely generating the negative ions and cleaning indoor air, without regard to a state of indoor air. Even when indoor air is relatively seriously polluted by some contaminants such as cigarette smoke, dust, etc., the air cleaning element 7 operates uniformly without regard to a pollution state. Thus, because the air cleaning element 7 does not operate in correspondence with the pollution level of indoor air, it does not effectively clean indoor air.

Particularly, the above conventional air cleaning control apparatus has the DC high-voltage generator 5, but it is not possible to easily control characteristics of the DC high-voltage generator 5. For this reason, even though the DC high-voltage generator 5 is used, it is difficult to easily generate ozone below a predetermined limit value using the air cleaning element 7. Consequently, even though ozone has a high sterilization effect, because ozone is not easily generated below the predetermined limit value, it is difficult to sterilize and clean indoor air.

SUMMARY OF THE INVENTION

Therefore, the present invention has been made in view of the above problems, and it is an object of the present invention to provide an apparatus and method for controlling air cleaning, wherein, an AC voltage and the AC frequency applied to an air cleaning element by an AC high-voltage generator depending on the pollution level of indoor air are adequately controlled, and it is possible to easily generate negative ions and ozone below a limit value depending on a state of indoor air, thereby increasing air cleaning performance to sterilize and clean contaminants more efficiently.

In accordance with an aspect of the present invention, the above and other objects can be accomplished by the provision of an apparatus for controlling air cleaning, the apparatus comprising: an air cleaning element for generating negative ions and ozone using plasma discharge, and cleaning air using the negative ions and ozone; an AC high-voltage generator for generating an AC high-voltage, and supplying the AC high-voltage to the air cleaning element; and a control unit for varying at least one of the AC voltage and AC frequency applied to the air cleaning element by the AC high-voltage generator depending on a state of indoor air being cleaned by means of the air cleaning element.

Preferably, the apparatus further comprises a rectifier for rectifying an AC voltage into a DC voltage with a fixed voltage and supplying the rectified DC voltage to the AC high-voltage generator.

Preferably, the apparatus further comprises a pollution level measuring instrument for measuring the pollution level of indoor air and supplying a pollution level signal to the control unit.

Preferably, the control unit raises the AC voltage or the AC frequency applied to the air cleaning element when the pollution level of indoor air is a high level, and the control unit lowers the AC voltage or the AC frequency applied to the air cleaning element when the pollution level of indoor air is a low level.

Preferably, the air cleaning element includes a discharge electrode and a ground electrode, the discharge electrode being formed on an upper surface of an insulating dielectric substrate with a substantially rectangular shape, the ground electrode being formed on a bottom surface opposite the upper surface.

Preferably, the discharge electrode is formed to expose a supply terminal for supplying an input voltage of the AC high-voltage generator, and the ground electrode is formed to expose a ground terminal which is connected with a ground circuit.

In accordance with another aspect of the present invention, there is provided a method for controlling air cleaning, the method comprising the steps of: a) measuring and determining the pollution level of indoor air; b) raising an AC voltage or an AC frequency applied to an air cleaning element by an AC high-voltage generator when the pollution level of indoor air is over a predetermined level; and c) lowering the AC voltage or the AC voltage's frequency applied to an air cleaning element by an AC high-voltage generator when the pollution level of indoor air is below the predetermined level.

Preferably, a determination result for the pollution level is divided into high, medium and low levels depending on the pollution level, and a magnitude of the AC voltage or the AC frequency is divided into large, medium and small depending on the determination result.

In a feature of the present invention, because an AC voltage and an AC frequency applied to the air cleaning element by the AC high-voltage generator depending on the pollution level of indoor air are adequately controlled, it is possible to effectively generate negative ions while minimizing ozone generation to an acceptable level depending on a state of indoor air, thereby increasing performance of an air cleaning so as to sterilize and clean airborne contaminants still more efficiently.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Now, preferred embodiments of the present invention will be described in detail with reference to the annexed drawings.

Figure 1:
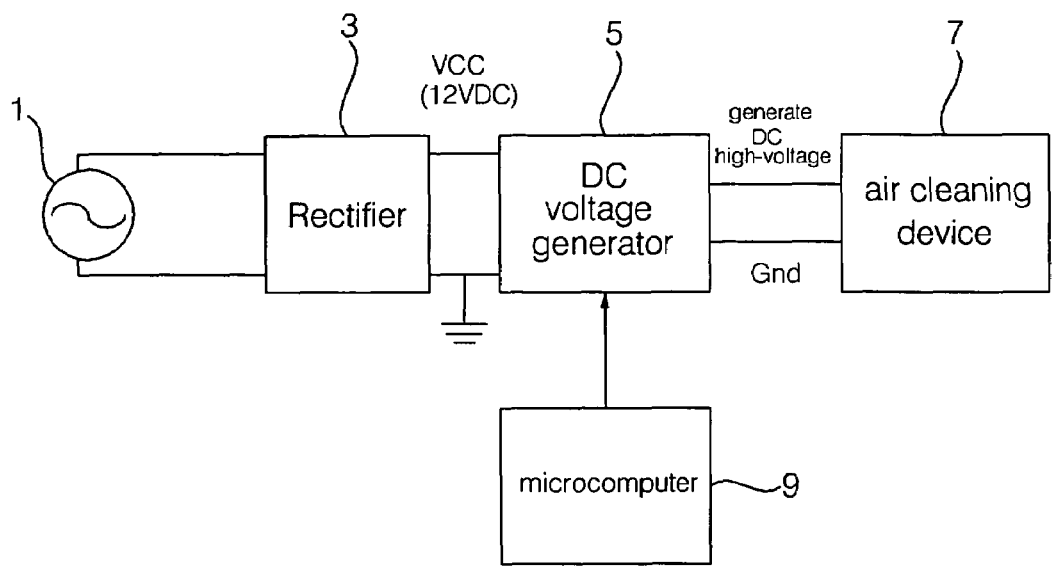
FIG. 1 is a block diagram showing the construction of a conventional air cleaning control apparatus.
Figure 2:
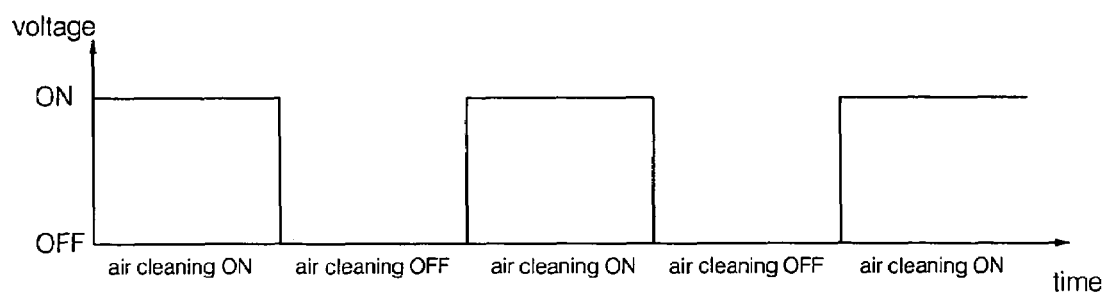
FIG. 2 is a graph illustrating an operating control state of the conventional air cleaning control apparatus.
Figure 3:
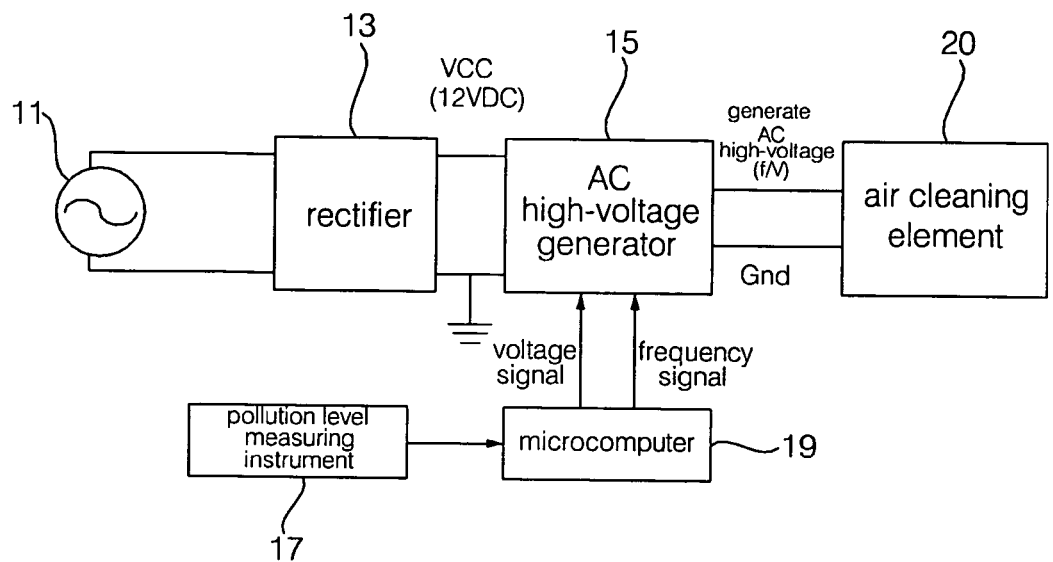
FIG. 3 is a block diagram showing the construction of an air cleaning control apparatus according to the present invention.
Figure 4:
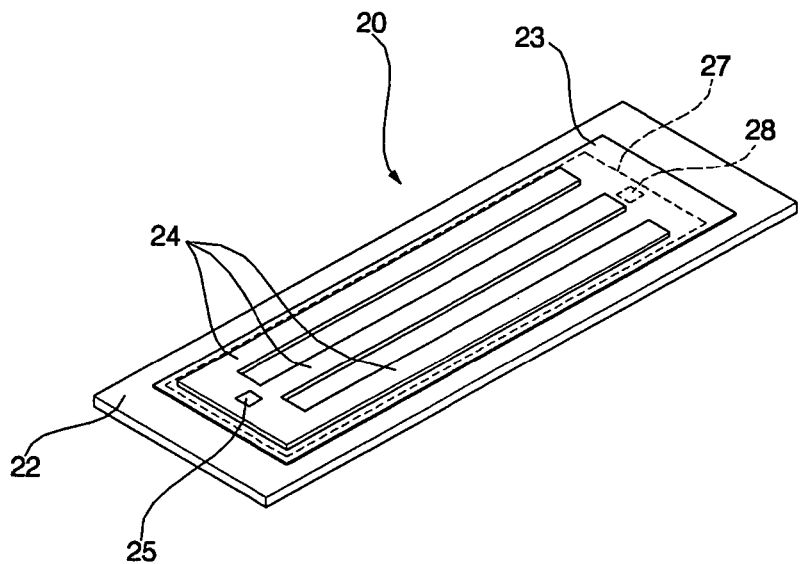
FIG. 4 is a perspective view illustrating an air cleaning element used in the present invention.

FIG. 3 is a block diagram showing the construction of an air cleaning control apparatus according to the present invention, and FIG. 4 is a perspective view illustrating an air cleaning element used in the present invention.

The air cleaning control apparatus according to the present invention includes, as shown in FIG. 3, an air cleaning element 20 for generating negative ions and ozone using plasma discharge and sterilizing and cleaning indoor air, an AC high-voltage generator 15 for applying an AC voltage to the air cleaning element 20, and a control unit such as a microcomputer 19 for varying either the AC voltage or an AC frequency, or both the AC voltage and the AC frequency which are applied to the air cleaning element 20 by the AC high-voltage generator 15, depending on a state of indoor air being cleaned by means of the air cleaning element 20.

The air cleaning element 20 includes, as shown in FIG. 4, a discharge electrode 24 and a ground electrode 27. The discharge electrode 24 is formed on an upper surface of an insulating dielectric substrate 22 with a substantially rectangular shape. The ground electrode 27 is formed on a bottom surface opposite the upper surface. The discharge electrode 24 and the ground electrode 27 are protected by a protective film 23 coated on both surface sides of the insulating dielectric substrate 22.

The discharge electrode 24 is formed to expose a supply terminal 25 for supplying an input voltage of the AC high-voltage generator 15. The ground electrode 27 is formed to expose a ground terminal 28 which is connected with a ground circuit.

The AC high-voltage generator 15 is formed, as shown in FIG. 3, to supply a voltage by way of the rectifier 13, the rectifier 13 rectifying the AC voltage such as a commercial voltage, etc., into a DC voltage, for example, a 12V DC voltage.

The AC high-voltage generator 15 applies the AC voltage to the air cleaning element 20, wherein the AC voltage is possible to control due to characteristics thereof. When a high-voltage over a predetermined voltage is applied to the air cleaning element 20, it is possible to generate negative ions as well as ozone having an excellent capability for sterilizing contaminants. In addition, when the AC voltage or the AC frequency applied to the air cleaning element 20 is varied, it is possible to adequately control ozone generation as well.

The microcomputer 19 is formed to receive a pollution measurement signal transmitted from a pollution measuring instrument 17 which includes a pollution level sensor, etc., the pollution measuring instrument 17 measuring a state of indoor air pollution.

In the case where the pollution level of indoor air is measured by the pollution measuring instrument 17, when the pollution level of indoor air is high, the microcomputer 19 raises the AC voltage and the AC frequency applied to the air cleaning element 20. While the pollution level of indoor air is low, the microcomputer 19 lowers the AC voltage and the AC frequency applied to the air cleaning element 20.

Consequently, the above microcomputer 19 controls the above AC high-voltage generator 15 so that the air cleaning element 20 generates ozone and negative ions. The concrete control procedures will be explained as follows.

Figure 5:
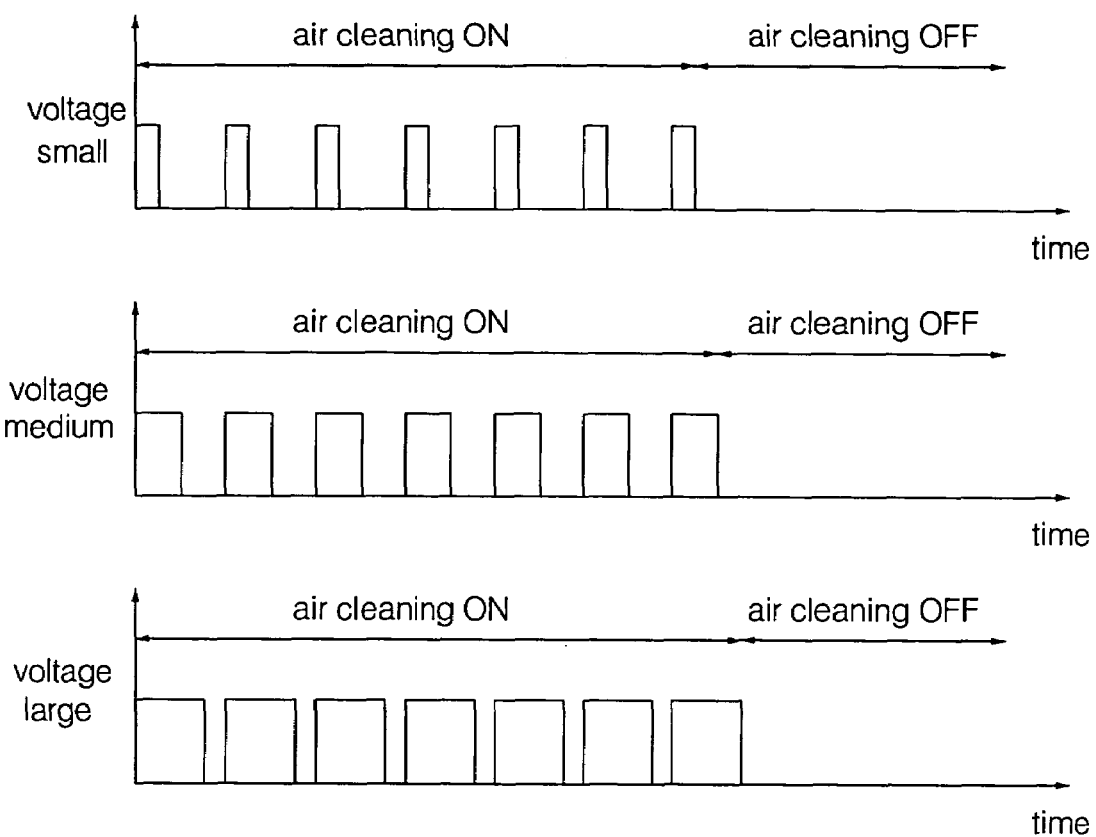
FIG. 5 is a graph illustrating AC voltage control signals in an air cleaning control apparatus according to the present invention.
Figure 6:
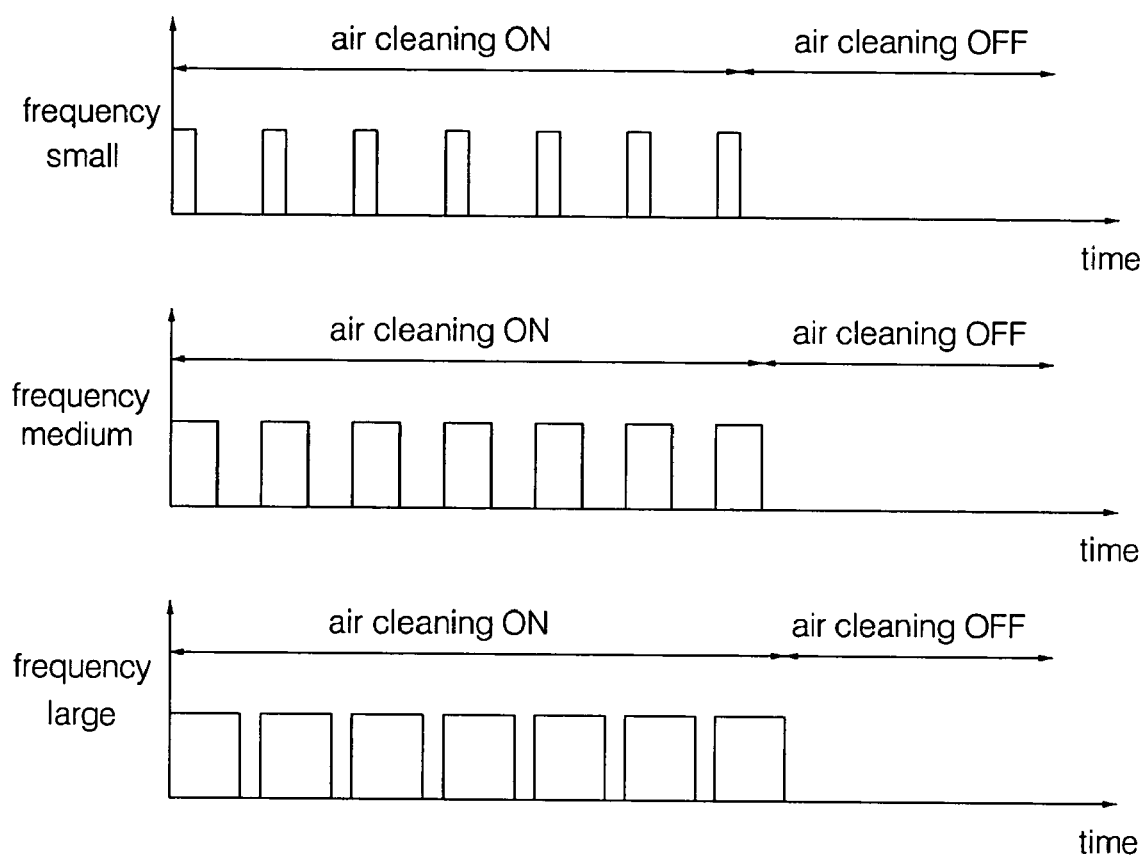
FIG. 6 is a graph illustrating frequency control signals in an air cleaning control apparatus according to the present invention.
Figure 7:
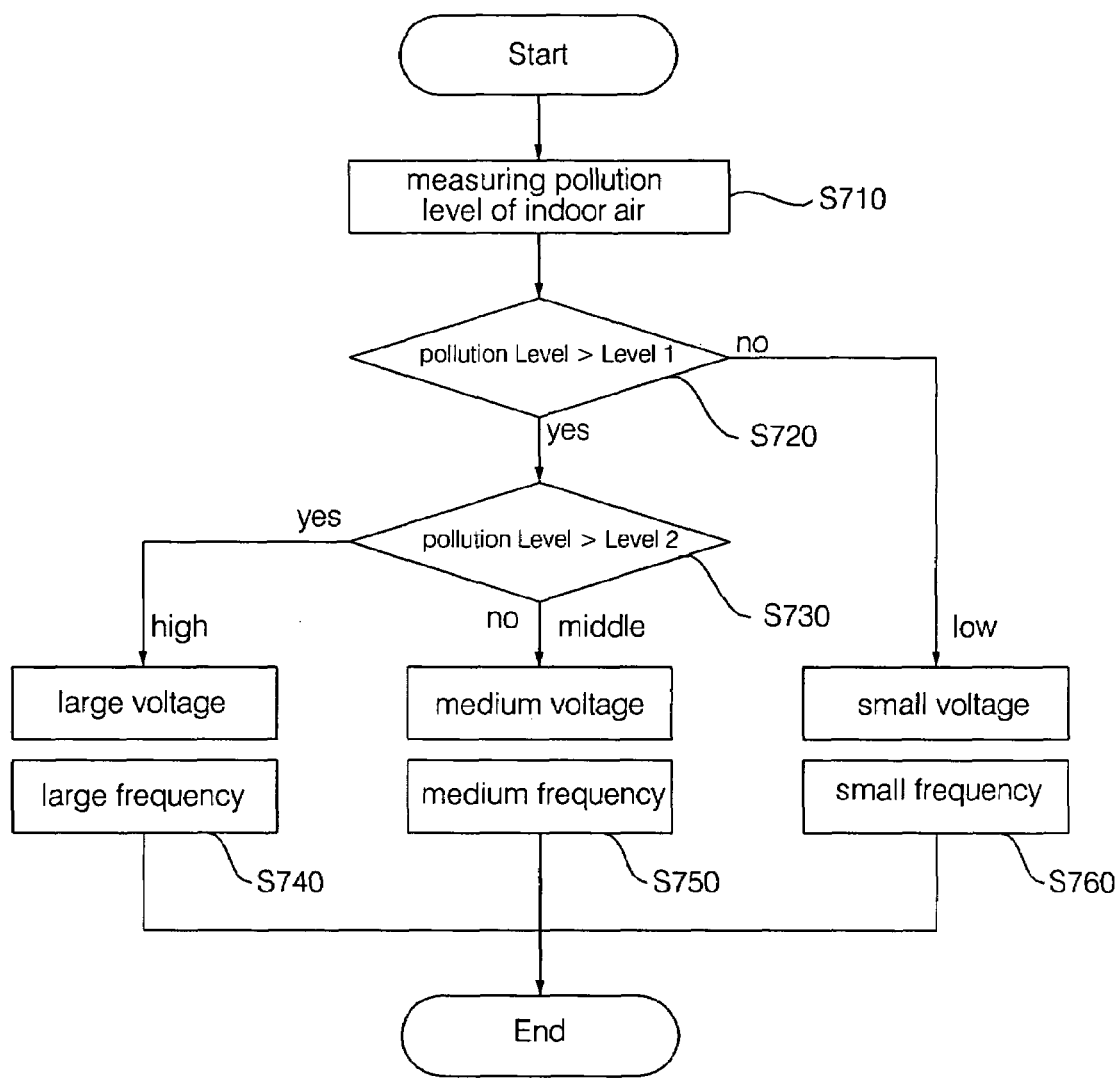
FIG. 7 is a flowchart illustrating a control method using an air cleaning control apparatus according to the present invention.

FIG. 5 is a graph illustrating AC voltage control signals in an air cleaning control apparatus according to the present invention, FIG. 6 is a graph illustrating frequency control signals in an air cleaning control apparatus according to the present invention, and FIG. 7 is a flowchart illustrating a control method using an air cleaning control apparatus according to the present invention.

To begin with, referring to FIG. 3, when the air cleaning control apparatus is operated, a 220V AC voltage as a commercial voltage 11 is rectified into a 12V DC voltage by the rectifier 13. Then, the DC voltage is supplied to an AC high-voltage generator 15.

The pollution level measuring instrument 17 measures the pollution level of indoor air (S710), and transmits a pollution level signal. The microcomputer 19 receives the pollution level signal from the pollution level measuring instrument 17, and determines the pollution level of indoor air.

The microcomputer 19 determines whether the pollution level of indoor air is over a predetermined level 1 (S720). When the pollution level of indoor air is below the predetermined level 1 the AC voltage or the AC frequency is set to a control level of "small" (S760).

In addition, when the pollution level of indoor air is over the predetermined level 1, the microcomputer 19 determines whether the pollution level of indoor air is over a predetermined level 2 (S730). When the pollution level of indoor air is over the predetermined level 1 and below the predetermined level 2, the AC voltage or the AC frequency is set to a control level of "medium" (S750). While the pollution level of indoor air is over the predetermined level 2, the AC voltage or the AC frequency is set to a control level of "large" (S740).

That is, when the microcomputer 19 determines that the pollution level of indoor air is over a predetermined level, it controls the AC high-voltage generator 15 so that the AC voltage and the AC frequency applied to the air cleaning element 20 by the AC high-voltage generator 15 may be raised.

Meanwhile, when the microcomputer 19 determines that the pollution level of indoor air is below the predetermined level, it controls the AC high-voltage generator 15 so that the AC voltage and the AC frequency applied to the air cleaning element 20 by the AC high-voltage generator 15 may be lowered.

Therefore, when the AC high-voltage generated by the AC high-voltage generator 15 depending on the above pollution level is applied to the air cleaning element 20, the air cleaning element 20 generates ozone and negative ions by plasma discharge. Consequently, the negative ions and ozone can sterilize and clean airborne harmful.

Referring to FIGS. 5 to 7, the air cleaning control method will be more concretely explained as follows.

The pollution level determined by the above microcomputer 19 is divided into control levels of "high", "medium" and "low", depending on the pollution state. In addition, the microcomputer 19 determines that a magnitude of the AC voltage or the AC frequency applied to the air cleaning element 20 by the AC high-voltage generator 15, is a control level of "large", "medium" or "small", and controls the AC voltage or the AC frequency.

That is, referring to FIGS. 5 and 7, in the case where the AC voltage may be controlled by a Pulse Width Modulation (PWM) method, when a pollution environment of indoor air determined by the microcomputer 19 is the worst case, in order to rapidly sterilize and clean a number of contaminants included in indoor air, the AC voltage applied to the air cleaning element 20 by the AC high-voltage generator 15 is determined as a control level of "large", thereby the air cleaning element 20 cleans indoor air.

In addition, when the pollution environment of indoor air determined by the microcomputer 19 is better than the above worst case, the AC voltage applied to the air cleaning element 20 by the AC high-voltage generator 15 is determined as a control level of "medium" or "small" depending on the pollution level of indoor air, thereby the air cleaning element 20 cleans indoor air.

Meanwhile, referring to FIGS. 6 and 7, in the same method as the above described method, in the case where the AC frequency may be controlled by the PWM method, when a pollution environment of indoor air determined by the microcomputer 19 is the worst case, in order to rapidly sterilize and clean a number of contaminants included in indoor air, the AC frequency applied to the air cleaning element 20 by the AC high-voltage generator 15 is determined as a control level of "large", thereby the air cleaning element 20 cleans indoor air.

In addition, in the same method as the above described method, when a pollution environment of indoor air determined by the microcomputer 19 is better than the above worst case, the AC frequency applied to the air cleaning element 20 by the AC high-voltage generator 15 is determined as a control level of "medium" or "small", thereby the air cleaning element 20 cleans indoor air.

Consequently, in the case where the AC high-voltage is differently applied to the air cleaning element 20 depending on the pollution level of indoor air, the amount of the plasma discharge generated in the air cleaning element 20 is varied, thereby it is possible to easily generate ozone and negative ions depending on the pollution level of indoor air.

Particularly, above a certain level ozone is toxic to humans. Thus, the amount of ozone and negative ions generated in the air cleaning element 20 must be adequately controlled depending on the pollution level. In addition, it is preferred that the magnitude of the AC voltage and the AC frequency applied to the air cleaning element 20 be determined as a control level of "large", below the limit value of ozone.

As apparent from the above description, the present invention provides an apparatus and method for controlling air cleaning, wherein, because an AC voltage and an AC frequency applied to the air cleaning element by the AC high-voltage generator depending on the pollution level of indoor air are adequately controlled, it is possible to effectively generate negative ions while minimizing ozone generation to an acceptable level depending on a state of indoor air, thereby increasing a performance of an air cleaning so as to sterilize and clean airborne contaminants more efficiently.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for controlling air cleaning, the apparatus comprising:
    an air cleaning element for generating negative ions and ozone using plasma discharge, and cleaning air using the negative ions and ozone;
    an AC high-voltage generator for generating an AC high-voltage and an AC frequency, and supplying the AC high-voltage and the AC frequency to the air cleaning element;
    a rectifier for rectifying an AC voltage into a DC voltage with a fixed voltage and supplying the rectified DC voltage to the AC high-voltage generator; and
    a control unit for varying at least one of the AC voltage and AC frequency applied to the air cleaning element by the AC high-voltage generator depending on a state of indoor air being cleaned by means of the air cleaning element.

2. The apparatus as set forth in claim 1, further comprising a pollution level measuring instrument for measuring a pollution level of indoor air and supplying a pollution level signal to the control unit.

3. The apparatus as set forth in claim 2, wherein, the control unit controls the AC voltage or the AC frequency applied to the air cleaning element to be relatively heightened when the pollution level of indoor air is a high level, and the control unit controls the AC voltage or the AC frequency applied to the air cleaning element to be relatively lowered when the pollution level of indoor air is a low level.

4. The apparatus as set forth in claim 1, further comprising a pollution level measuring instrument for measuring a pollution level of indoor air and supplying a pollution level signal to the control unit.

5. The apparatus as set forth in claim 4, wherein, the control unit controls the AC voltage or the AC frequency applied to the air cleaning element to be relatively heightened when the pollution level of indoor air is a high level, and the control unit controls the AC voltage or the AC frequency applied to the air cleaning element to be relatively lowered when the pollution level of indoor air is a low level.

6. The apparatus as set forth in claim 1, wherein the air cleaning element includes a discharge electrode and a ground electrode, the discharge electrode being forming on an upper surface of an insulating dielectric substrate with a substantially rectangular shape, the ground electrode being formed on a bottom surface opposite the upper surface.

7. The apparatus as set forth in claim 5, wherein, the discharge electrode is formed to expose a supply terminal for supplying an input voltage of the AC high-voltage generator, and the ground electrode is formed to expose a ground terminal which is connected with a ground circuit.

8. A method for controlling air cleaning, the method comprising the steps of:
   a) measuring and determining the pollution level of indoor air;
   b) controlling an AC voltage and an AC frequency applied to an air cleaning element by an AC high-voltage generator, to be relatively heightened when the pollution level of indoor air is over a predetermined level; and
   c) controlling the AC voltage and the AC frequency applied to an air cleaning element by an AC high-voltage generator, to be relatively lowered when the pollution level of indoor air is below the predetermined levels,
   wherein a determination result for the pollution level is divided into high, medium, and low depending on the pollution level, and a magnitude of the AC voltage or the AC frequency is divided into large, medium, and small depending on the determination result.

* * * * *